United States Patent
Abraham-Fuchs et al.

(10) Patent No.: US 7,326,058 B2
(45) Date of Patent: Feb. 5, 2008

(54) METHOD AND SYSTEM FOR SUPPORTING THERAPY PLANNING WHEN CREATING A TRAINING PROGRAM

(75) Inventors: Klaus Abraham-Fuchs, Erlangen (DE); Uwe Eisermann, Erlangen (DE); Niels Richter, Thurnau (DE); Robert Setz, Rednitzhembach (DE)

(73) Assignee: Siemens Aktiengesellschaft, München ( * ) Notice: Subject to any disclaimer, the term of this patent is extended or adjusted under 35 U.S.C. 154(b) by 762 days.

(21) Appl. No.: 10/611,933

(22) Filed: Jul. 3, 2003

(65) Prior Publication Data

US 2004/0038190 A1   Feb. 26, 2004

(30) Foreign Application Priority Data

Jul. 3, 2002   (EP) .................................. 02014702

(51) Int. Cl.
*G09B 19/00* (2006.01)
(52) U.S. Cl. .................................................... 434/236
(58) Field of Classification Search ................ 434/262, 434/258, 236, 247, 273; 600/300, 301
See application file for complete search history.

(56) References Cited

U.S. PATENT DOCUMENTS

| | | | |
|---|---|---|---|
| 5,135,399 A | 8/1992 | Ryan | 434/236 |
| 5,524,645 A | 6/1996 | Wills | 128/898 |
| 5,764,923 A | 6/1998 | Tallman et al. | 395/203 |
| 5,961,332 A * | 10/1999 | Joao | 434/236 |
| 6,606,480 B1 * | 8/2003 | L'Allier et al. | 434/362 |
| 6,875,020 B2 * | 4/2005 | Niddrie et al. | 434/236 |
| 2003/0118978 A1 * | 6/2003 | L'Allier et al. | 434/362 |
| 2003/0191777 A1 * | 10/2003 | Lumsden et al. | 707/104.1 |
| 2004/0023197 A1 * | 2/2004 | Abraham-Fuchs et al. | 434/236 |

FOREIGN PATENT DOCUMENTS

| | | |
|---|---|---|
| WO | WO 01/26548 A1 | 4/2001 |
| WO | WO 02/41231 A2 | 5/2002 |

\* cited by examiner

*Primary Examiner*—Robert E Pezzuto
*Assistant Examiner*—Frank M. Leiva
(74) *Attorney, Agent, or Firm*—Alexander J. Burke

(57) ABSTRACT

A method and a system are for supporting therapy planning when creating a training program. The method involves a capability profile for a patient and also a first and a second database being provided. The first database contains a plurality of skills and an allocation of minimum prerequisites for capabilities required for the respective skills. The second database contains a plurality of skills with expert rules relating to the selection of exercises and/or of capabilities to be treated and also their order and/or weighting for the purpose of acquiring the respective skills taking into account existing capabilities and capability deficits. A data processing station automatically evaluates the capability profile for at least one patient skill which is to be treated by reverting to the first database in order to ascertain the existing capabilities and capability deficits, and reverts to the second database, taking into account the expert rules, in order to select exercises and/or capabilities which are to be treated and to output them with information about the weighting and/or order for carrying out training. The present method and the associated system reduce the physician's or therapist's time involvement when creating a training program individually tailored to the patient.

39 Claims, 3 Drawing Sheets

| Patient A | |
|---|---|
| Capability | Deficit |
| Stamina | 10% |
| Balance | 30% |
| Reaction | 10% |
| Mobility in left lower leg | 60% |
| Strength in left lower leg | 80% |
| ............ | |

Fig. 1

| Patient A | |
|---|---|
| Skill | Deficit |
| Washing without help | 30% |
| Eating without help | 10% |
| Driving | 100% |
| Buying daily necessities | 60% |
| ............ | |

Fig. 2

| Patient A | | Allocation of the capabilities required for a skill | | |
|---|---|---|---|---|
| Skill | Capability 1 Talking | Capability 2 Swallowing | Capability 3 eye-to-hand coordination | ............ |
| Washing without help | No | No | Yes | |
| Eating without help | No | Yes | Yes | |
| Driving | No | No | Yes | |
| Telephoning | Yes | No | Yes | |
| ............ | ............ | | | |

Fig. 3

| Patient A | |
|---|---|
| Therapy module | Target capabilities receiving therapy |
| Ergometer training | Cardio-circulatory stress |
| Balance exercise | Capability 2 |
| Reaction training package A from computer training from company Y | Capability 3 |
| Exercise No. 32 from exercise series Z (mobility in lower leg) | Capability 4 |
| Exercise No. 64 from exercise series Z (strength in lower leg) | Capability 5 |
| ............ | ............ |

Fig. 4

METHOD AND SYSTEM FOR SUPPORTING THERAPY PLANNING WHEN CREATING A TRAINING PROGRAM

The present application hereby claims priority under 35 U.S.C. §119 on European patent application number EP 02014702.1 filed Jul. 3, 2002, the entire contents of which are hereby incorporated herein by reference.

FIELD OF THE INVENTION

The present invention generally relates to a method and a system for supporting therapy planning when creating a training program for rehabilitating a patient.

BACKGROUND OF THE INVENTION

Serious illnesses such as stroke, heart attack or Alzheimer's disease or serious operations such as the insertion of joint implants or the performance of an amputation cause most patients to have different deficits in physical and mental performance. These deficits are generally the result of the weakening or complete failure of a region of the brain or of a muscle. Combinations of these also frequently arise.

Thus, by way of example, a region of the brain which is responsible for controlling a muscle or a number of muscles in functional chains can be damaged. As a result, the affected muscles degenerate. Thus, they are no longer able to be used properly. Such mental or physical restrictions are referred to in the medical vernacular as capability deficits, which can be split into various areas of capability. Thus, one known classification makes the following exemplary distinctions:

- motor capabilities such as strength, stamina, mobility, balance, reaction, orientation, differentiation, accommodation, speech motor functions;
- intellectual/cognitive capabilities such as attention, memory, planning, comprehension of speech, communication, vision;
- organic/physical capabilities such as reduction of organ performance;
- social capabilities such as ability to communicate and participate;
- emotional capabilities such as the capability to develop self-esteem.

Some capabilities also require interplay between motor functions and cognitive functions. Thus, by way of example, the activity of climbing stairs requires strength and balance as motor capabilities and attention and spatial awareness as cognitive capabilities.

Very often, a patient does not have a single deficit in one capability category but rather has a combination of a plurality of deficits in a more or less serious form. The aim of a therapeutic measure, which is normally performed as part of a rehabilitation process, is to restore the capabilities or to reduce the existing deficits as far as possible. At the start of the rehabilitative measure, this generally involves all the patient's capability deficits being recorded using known methods of measurement, observation and questioning, and their extent being documented. This recording process is also referred to as staging the patient. Depending on the methods of measurement used, the result of this staging process is quantitative, for example a percentage of visual capability or an indication of the degree of mobility in the upper arm, or qualitative, for example a classification of the capability restriction as severe, intermediate or slight. One example of an established method of measurement for staging numerous neurological, cognitive and psychological capabilities is the "Wiener test series" from the company Schuhfried.

The result of this initial examination is ideally a cross-discipline capability report which can be presented in the form of a capability profile. In this context, a capability profile is defined as a list of all relevant capabilities and an association between the degree of the restriction in these capabilities for this patient and the time at which the information was collected.

In addition to the term capabilities, the term skill is also used in the medical vernacular. In the context of a medical rehabilitation measure, a skill is understood to mean a complex action but one which is self-contained and can be delimited with respect to other actions. A skill requires interplay between a plurality of capabilities. In particular, the term skill in the context of rehabilitation refers to activities of daily living (ADL) which are a primary prerequisite for independent, autonomous living. Examples of such skills are eating, dressing, washing, showering, climbing stairs, etc. The performance of such skills is also recorded in standardized questionnaires and is quantified as an ADL index. Although rehabilitation directly involves the training of capabilities, the actual aim is to reacquire skills.

To improve a skill in a patient, it is normally necessary to perform a plurality of exercises relating to different capabilities relevant to the skill. The order and weighting of these exercises depends, inter alia, on the extent of the respective capability deficits in the patient. When creating a training program, the physician or therapist needs to take into account these dependencies and create a suitable training program, normally including a plurality of exercises, on the basis of his experience.

SUMMARY OF THE INVENTION

An object of an embodiment of the present invention is to specify a method and a system for supporting therapy planning when creating a training program. Preferably, the system and method reduce the time involvement for the competent physician or therapist. In particular, they allow the creation of a training program for acquiring the skills as quickly as possible.

At least one embodiment of the present method for supporting therapy planning when creating a training program involves a current capability profile for the patient and a first and a second database being provided. The first database contains a plurality of skills and an allocation of minimum prerequisites for capabilities required for the respective skill. The second database contains a plurality of skills with expert rules relating to the selection of exercises and/or of capabilities to be treated and also their order and/or weighting for the purpose of acquiring the respective skills taking into account existing capabilities and capability deficits. A data processing station automatically evaluates the patient's capability profile for at least one patient skill which is to be treated by reverting to the first database in order to ascertain the existing capabilities and capability deficits relevant to the skill which is to be treated. On the basis of this evaluation, the data processing station reverts to the second database, taking into account the expert rules, in order to select exercises and/or capabilities which are to be treated and to output them with information about the weighting and/or order for carrying out training, preferably together with the respective skill which is to be treated.

The respective skill which is to be treated can be input by the user, for example. Preferably, however, the one or more skills to be treated are automatically ascertained by the data processing station from a skills profile for the patient which is provided for carrying out the method. In this context, the skills in need of treatment are ascertained on the basis of the extent indicated in the skills profile or the deficit of the respective skill. If this extent of the skill is below or the deficit is above a prescribable value relative to a comparative person's 100% skill, then this skill is classified as being in need of treatment. The patient's capability profile and skills profile are preferably provided by way of a database from which they are retrieved by the data processing station. Naturally, this can involve the use either of different databases for the skills profile and the capability profile or of a joint database for the two profiles.

As a result of the automatic evaluation of the capability profile and possibly of the skills profile and the automatic selection of exercises and their weighting and/or order by the data processing station, the user, i.e. the physician or therapist, is provided with a proposal for creating a training program which is already individually tailored to the patient's initial situation. In this case, the expert rules in the second database are designed such that the respective skills are acquired as quickly as possible with the training program. The training program proposed to the physician in the form of one or more exercises and the order and/or weighting thereof thus ensures that the patient reacquires the corresponding skills in the shortest possible time period. Rapid success of treatment in turn raises the patient's confidence in life and his compliance. On the whole, the proposed method and system are thus used to increase the patient's quality of life with the available therapy options as far as possible in the shortest possible time. Naturally, the user is also able to modify the training program proposed by the data processing station if he thinks this necessary on the basis of more extensive experience.

The expert rules held in the second database can be in a relatively simple form, for example by virtue of the difficulty level of the exercises being matched to the respective extent of the deficit. In addition, the time involvement specified for each selected exercise can be chosen with a weighing based on the percentage deficit of the associated capabilities. If there are two deficits of 80% and 20%, respectively, for example, then the rules can likewise choose the duration of the associated exercises to be 80% and 20%. Preferably, the rules are in a more complex form, however, and include physicians' experience or general medical experience for the treatment of skills. In particular, the rules should take into account the extent of the individual deficits existing in each case.

In another embodiment of the present method, a further database is provided which contains a plurality of skills and a prioritization for the skills. This prioritization indicates in what order the respective skills deficits need to be treated. In this context, the prioritization can be created taking into account the medical necessity, restrictive constraints based on the patient's personal circumstances, or personal preferences of the patient. This prioritization can be performed automatically in the first step by using both medically recognized criteria and other criteria applicable to the normal average for a region's population.

One medical criterion is, by way of example, the necessity of a skill to life, such as breathing without technical accessories, swallowing etc. The next priority level can be the acquisition of a skill necessary to life without the assistance of third parties, such as eating independently. Further priority levels can then cover imperatively necessary tasks of daily living, such as speaking or other ways of communication, going to the toilet, dressing, washing, preparing food etc.

Finally, further categories covered in the prioritization can also be necessary tasks for which dependency on third parties significantly restricts quality of life, such as shopping, withdrawing money, climbing stairs, or activities which are a fundamental part of the quality of life, such as driving a car, telephoning, taking a bath, operating technical equipment etc. Particularly in the last two categories of prioritization, standards from medical experience or beyond a popular average are useful. This can involve preferences and wishes of the patient, which the treating physician or therapist can ascertain through questioning.

In addition, the physician will also want to alter priorities as a result of existing constraints making it seem as though, by way of example, there is little prospect of a skill of relatively high priority being attained again, while there is good prospect of another of relatively low priority being able to be attained in a feasible period of time. Such constraints can be, by way of example, the patient's age, intelligence, physical constitution etc. The physician will then presumably assign a second skill an individually higher priority in the patient's treatment plan. For this reason, automated prioritization, or prioritization prescribed by the database, of the order of the skills deficits which are to be treated is followed by their being the opportunity to alter the prioritization or priority list interactively. In this embodiment of the invention, the data processing station selects the skill with the highest priority and outputs corresponding exercises and their weighting and/or order which are suitable for treating the skill in question.

In one particularly preferred embodiment of the present method and of the associated system, a current capability and, if appropriate, skills profile for the patient is repeatedly provided in the course of therapy in order to automatically generate proposals for modifying the training program by reverting to the expert rules in the corresponding database again in the event of individual capabilities and capability deficits changing. The respective current capability profile is preferably collected at regular intervals and the corresponding database content is changed. For telemedical forms of care, such collection can, if appropriate, also take place by virtue of data communication from the patient's home to the clinic, for example by measuring the success of exercises in computer-based training programs or by virtue of computer-based collection of questionnaires relating to quality of life.

The automatic collection of the capability profile which is possible in this context is effected using the training computer provided in the patient's domestic environment. If there are any altered capability profiles, the evaluation already described and the output of exercises with their weighting and/or order are repeated by reverting to the expert rules. In this way, the prescribed training program can be continually adjusted, always with the aim of optimizing the treatment of individually prioritized skills deficits. In particular, it is advantageous to measure, for a plurality of capability deficits treated simultaneously, the progress of treatment for each capability, i.e. the reduction in the respective percentage deficit, and to compare the different capabilities.

The aim of the comparison and of the proposal, automatically derived therefrom, for modifying the training program is to achieve balanced progress of therapy in all capabilities. There are a number of reasons for this being a particularly useful method of quality control for the therapy. Thus, the actual aim is firstly to reacquire a particular skill. This requires all the capabilities being treated simultaneously to be reacquired. It is thus not useful for the success of treatment if some capabilities achieve very good progress while others are clearly left behind, since the actual aim of reacquiring the skill is then not achieved. In this case, the training program therefore needs to be shifted in favor of capabilities which exhibit less of an improvement.

The effect just described is frequently further enhanced by virtue of exercise successes providing the patients with increased motivation for those very capabilities which are less critical anyway. Another known effect of overtraining is learning by heart, i.e. reflex-like performance of the exercise task within the context of the exercise, without the same task being able to be retrieved equally well in another context, e.g. when the target skill is performed. As a result of continual repeated collection of the capability profile and, if appropriate, the skills profile and the corresponding evaluation and reassessment of the situation, the training program is respectively matched to the current situation in order to ensure that the target skill is acquired as quickly as possible.

This method in line with an embodiment explained above is used to provide automated monitoring of the progress of therapy and automated creation of proposals for modifying the training program, which involves balanced progress of all relevant capabilities being ensured with the aim of reacquiring a skill. The proposed method and system thus use repeated evaluation of the capability profiles to identify unbalanced therapy progress while a plurality of capability deficits undergo therapy at the same time, and automatically create a proposal for suitably modifying the training program.

The associated system for supporting therapy planning comprises a data processing station which is connected to the first and second databases. The data processing station contains a module for automatically evaluating a capability profile for a patient by reverting to the first database in order to ascertain the existing capabilities and capability deficits relevant to a skill which is to be treated and for selecting and outputting exercises and/or capabilities which are to be treated with information about the weighting and/or order for carrying out training for the skill which is to be treated by reverting to the second database and taking into account the expert rules.

In further embodiments of the present system, the data processing station is connected to one or more of the further databases, and the module is accordingly designed to carry out the method steps explained above.

BRIEF DESCRIPTION OF THE DRAWINGS

The present method and the associated system are explained once again below using an exemplary embodiment in conjunction with the drawings, without limiting the general concept of the invention. In the drawings:

FIG. 1 shows an example of a capability profile for a patient (in the form of an excerpt);

FIG. 2 shows an example of a skills profile for a patient (in the form of an excerpt);

FIG. 3 shows an example of a first database containing a plurality of skills and an allocation of minimum prerequisites for capabilities required for the respective skill;

FIG. 4 shows an example of a database with therapy modules or exercises and associated target capabilities which are trained using the respective exercise.

DETAILED DESCRIPTION OF THE PREFERRED EMBODIMENTS

Figure 5:
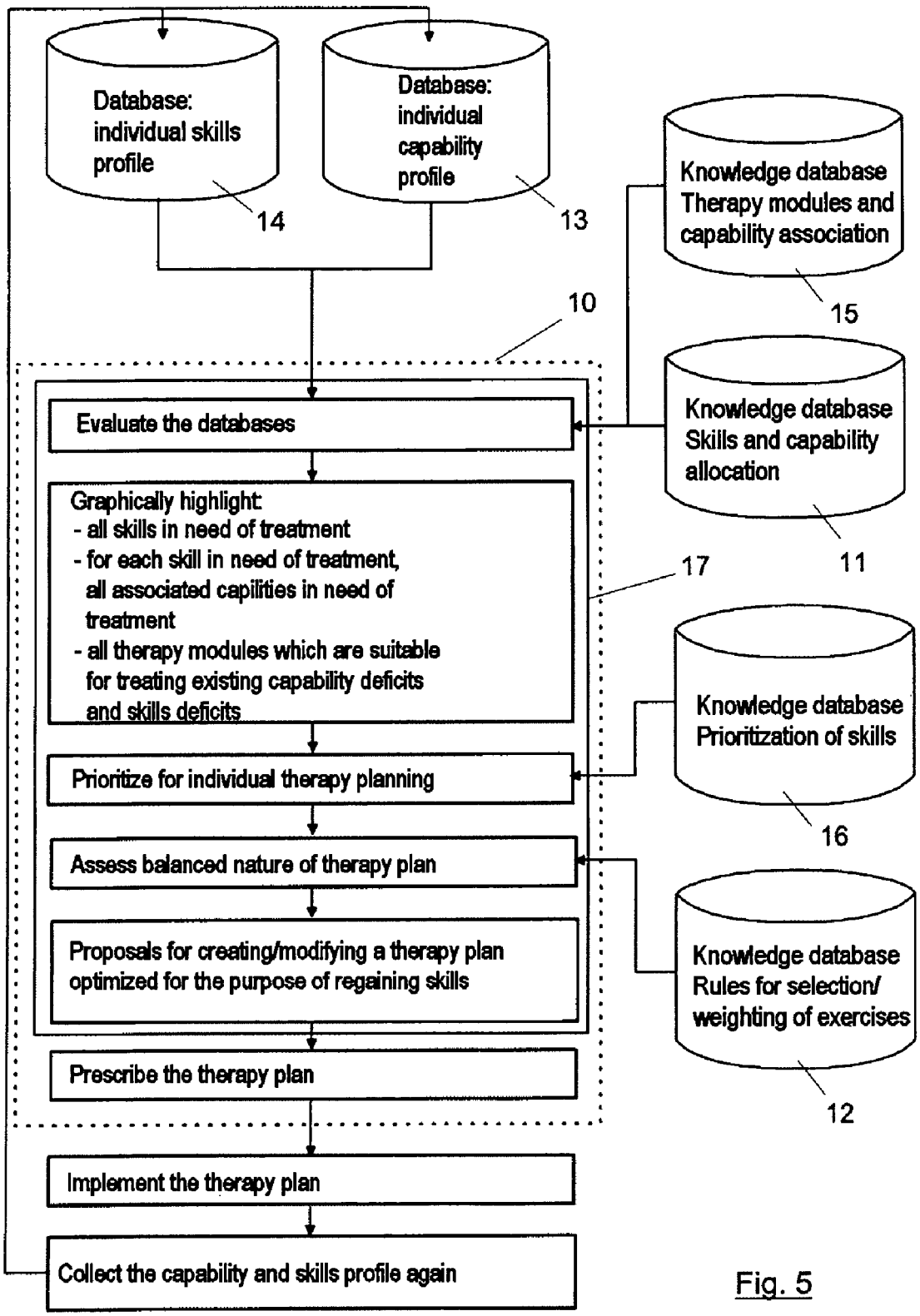
FIG. 5 shows an overview of the present method and of the associated system in an embodiment of the invention.

In the present exemplary embodiment, the process of creating a training program in therapy planning by a physician or therapist using the present method and the associated system in a specific embodiment is explained by way of example. The exemplary system includes a computer workstation (data processing station 10) for therapy planning and therapy progress control with a module 17 for automated evaluation of the data provided by databases. The data processing station 10 is connected to the various databases, from which the module 17 retrieves the necessary information. The basic equipment of this exemplary system includes a first knowledge database 11 with capabilities and an allocation of necessary capabilities, a knowledge database 12 with expert rules for selecting exercises and their order and/or weighting for treating different skills, and a database 13 with the individual capability profile of the patient.

An example of a capability profile as held in the corresponding database 13 is shown as an excerpt in FIG. 1. This capability profile comprises different capabilities, such as stamina, balance etc. with the respective deficit, i.e. the percentage by which the respective capability in this patient is reduced as compared with the 100% capability of a healthy comparative person.

The first knowledge database 11 contains a multiplicity of skills and also minimum prerequisites, associated with the respective skills, for capabilities required for the skill. An example of such an allocation is shown in FIG. 3. This illustration shows that to acquire the skill of eating without help, for example, the capability of speech is not necessary, whereas the capability of swallowing and eye-to-hand coordination are necessary prerequisites. The latter capabilities therefore need to be trained if they are not present in the patient to a sufficient degree. In addition, for each capability this database also contains an indication of the extent to which the capability needs to exist for the respective skill, if this extent is below 100%. This cannot be seen from FIG. 3.

Optionally, the present system can have further databases connected to the data processing station 10. Thus, a database 14 with an individual skills profile for the patient can be provided. The content of this database comprises the individual skills and the associated deficit, as illustrated in detail form by way of example with reference to FIG. 2. The module 17 in the data processing station 10 accesses this database 14 in order to retrieve the skills profile, and evaluates the skills profile in order to ascertain the skills to be treated for which the deficit is more than 0%, for example.

On the basis of the ascertained skills to be treated, the module 17 then reverts to the further databases 11, 12 available in all cases in order to automatically create a proposal for a training program, i.e. the individual exercises, the level of difficulty of the exercises and the order and/or weighting, particularly the length of time for the individual exercises, and to output it for the user on a monitor. The output can naturally also be provided in another way, for example using a printer.

Optionally, the present system can also have a third knowledge database 16 containing a prioritization for the skills in need of treatment. The module 17 then outputs either just one training program for the skill with the highest priority or a plurality of training programs in the order of the priorities of the skills which are to be treated.

In addition, a fourth knowledge database 15 can be provided which contains a plurality of therapy modules or exercises and an allocation of target capabilities treated with the respective therapy module. An example of such an allocation is shown in FIG. 4.

When using the present method or the associated system, the physician or therapist involved in therapy planning on the computer workstation 10 has access to all the therapy modules or exercises which are available to him for prescription. As a result of automatic evaluation of the databases connected to the data processing station 10, particularly of the database 13 with the capability profile, the first and second knowledge databases 11, 12 and possibly the databases 13 with the skills profile, optionally all the skills in need of treatment, for each skill in need of treatment all associated capabilities in need of treatment, and—when reverting to the fourth knowledge database 15—all the therapy modules which are suitable for treating existing capability deficits and skills deficits can be output or displayed in a first step.

The corresponding skills and capabilities can additionally be graphically highlighted. The present method does not require this display or output in all cases, however. Instead, reversion to the first and second knowledge databases 11, 12 allows the module 17 to automatically output a proposal for exercises and their order and/or weighting which, on the basis of the expert rules, results in an optimum, particularly a balanced, training program. If there are a plurality of skills deficits in need of treatment, reversion to the third knowledge database 16 with the prioritization initially allows output of just the proposal for the skill to be treated which has the highest prioritization or else a plurality of proposals in the order of the prioritization.

On the basis of this output by the data processing station 10, already taking into account the rules for the quickest possible acquisition of the skills which are to be treated, the physician or therapist can prescribe a training program individually tailored to the patient without any great time involvement. In this context, the physician or therapist can accept the proposed training program in identical form or may adjust or alter it as appropriate on the computer workstation.

When a training program has been prescribed, this exemplary embodiment involves the patient's capability profile and possibly skills profile being repeatedly collected again during the training program and being stored in the respective databases 13, 14. In this case, the module 17 in the computer workstation 10 checks the corresponding profiles for alterations and repeats the steps carried out for originally creating the training program, so that, if appropriate, an adjusted or altered training program is output. The physician or therapist can then take this adjusted training program as a basis for further training. This repeated therapy control automatically reacts directly to alterations which make it necessary to modify the training program, and the correspondingly modified training program is output. This allows the therapy to be optimized in order to acquire the skills as quickly as possible.

For the use of databases and graphical user interfaces on a computer workstation, the method illustrated by way of example and the associated system automatically provide the treating physician or therapist with proposals for creating a training program which allow the therapy planning to be optimized in terms of individual skills deficits, and, in particular, they ensure that the therapy for associated capability deficits is of a balanced nature.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for supporting therapy planning when creating a training program for patient rehabilitation, comprising:

providing a capability profile for a patient, a first database containing a plurality of patient physiological skills and cognitive skills supporting said physiological skills to be treated with a patient rehabilitation treatment plan and an allocation of minimum prerequisites for capabilities required for a respective patient physiological skill, and a second database, said second database containing a plurality of patient rehabilitation skills with expert rules relating to the selection of at least one of exercises and capabilities to be treated during said patient rehabilitation plan, and containing at least one of an associated order and weighting for the at least one of exercises and capabilities, for determining successful acquisition of said respective patient physiological skills, taking into account existing capabilities and capability deficits of said patient;

automatically evaluating, at a data processing station, the patient's capability profile for at least one patient skill which is to be treated by reverting to the first database to ascertain the existing capabilities and capability deficits;

selecting, by reverting to the second database and taking into account the expert rules, at least one exercise and capability to be treated; and outputting the at least one selected exercise and capability to be treated, with associated information about at least one of the weighting and order for incorporation into a patient rehabilitation treatment plan.

2. The method as claimed in claim 1, wherein a patient physiological skill is an activity associated with daily living for said patient enabling a patient to live an autonomous and independent life, and further comprising providing a rehabilitation skills profile for the patient from which the data processing station automatically ascertains patient rehabilitation skills, which are to be treated.

3. The method as claimed in claim 2, wherein at least one of the patient's capability and skills profile is retrieved from at least one of a third and a fourth database.

4. The method as claimed in claim 1, wherein at least one associated target capability identifying successful acquisition of said patient skill provided in said patient rehabilitation plan is automatically output by the data processing station for each exercise that is output.

5. The method as claimed in claim 4, wherein the at least one associated target capability is retrieved from another database, containing a plurality of exercises and an allocation of target capabilities which are trained when performing the respective exercise.

6. The method as claimed in claim 5, wherein a further database is provided which contains a plurality of patient physiological skills and a prioritization of the skills.

7. The method as claimed in claim 6, wherein the prioritization of the patient physiological skills in the further database is alterable by a user.

8. The method as claimed in claim 6, wherein the data processing station reverts to the further database for the purpose of automatically selecting exercises, usable to treat capabilities in need of treatment, which belong to, that patient physiological skill to be treated by said patient rehabilitation plan which has the highest prioritization.

9. The method as claimed in claim 1, wherein the expert rules in the second database, relating to at least one of the selection of exercises and capabilities to be treated and also their at least one of order and weighting, are designed for the fastest possible acquisition of the respective skills.

10. The method as claimed in claim 1, wherein the data processing station automatically outputs, for all at least one of exercises and capabilities to be treated, at least one of an associated organization unit and organization category which is responsible for at least one of carrying out the exercise and treating the capability.

11. The method as claimed in claim 1, wherein, in the course of therapy, a current capability profile for the patient is repeatedly provided for the purpose of automatically generating proposals for modifying the training program by reverting to the expert rules in the second database again when individual capabilities change.

12. A system for supporting therapy planning when creating a training program for patient rehabilitation, comprising:
   a data processing station, coupled to a first database containing a plurality of capabilities and an allocation of minimum prerequisites for capabilities required for a respective patient physiological skill and cognitive skill supporting said physiological skill, and coupled to a second database containing a plurality of patient physiological skills with expert rules relating to the selection of at least one of exercises and capabilities to be treated during said patient rehabilitation plan and also at least one of their order and weighting for determining successful acquisition of the respective patient skills taking into account existing capabilities and capability deficits; and
   a module for automatically evaluating a capability profile for a patient by reverting to the first database to ascertain the capabilities and, capability deficits existing for a patient physiological skill to be treated and for selecting and outputting at least one of exercises and capabilities to be treated for incorporation into a patient rehabilitation treatment plan with information about the at least one of weighting and order for carrying out training by reverting to the second database and taking into account the expert rules.

13. The system as claimed in claim 12, wherein the module automatically ascertains the patient's physiological skills to be treated on the basis of a skills profile for the patient.

14. The system as claimed in claim 13, wherein the data processing station is coupled to at least one of a third and a fourth database, from which the at least one capability and skills profile is retrievable.

15. The system as claimed in claim 12, wherein the data processing station is coupled to a another database containing a plurality of patient physiological skills and a prioritization for the patient physiological skills, and wherein the module is designed for automatically selecting exercises by reverting to another database, the exercises being able to be used to treat capabilities in need of treatment, which belong to, that skill to be treated which has the highest prioritization.

16. The system as claimed in claim 15, wherein the module allows the prioritization to be altered by the user.

17. The system as claimed in claim 12, wherein the module is designed for repeatedly retrieving the patient's capability profile in the course of therapy for the purpose of automatically generating proposals for modifying the training program by reverting to the expert rules in the second database again when individual capabilities change.

18. The system as claimed in claim 12, wherein the expert rules in the second database are created for the fastest possible acquisition of the respective skills.

19. The method as claimed in claim 3, wherein at least one associated target capability is automatically output by the data processing station for each exercise that is output.

20. The method as claimed in claim 19, wherein the at least one associated target capability is retrieved from a fifth database, containing a plurality of exercises and an allocation of target capabilities which are trained when performing the respective exercise.

21. The method as claimed in claim 7, wherein the data processing station reverts to the further database for the purpose of automatically selecting exercises, usable to treat capabilities in need of treatment which belong to that skill to be treated which has the highest prioritization.

22. The method as claimed in claim 20, wherein a sixth database is provided which contains a plurality of skills and a prioritization of the skills.

23. The method as claimed in claim 22, wherein the prioritization of the skills in the sixth database is alterable by a user.

24. The method as claimed in claim 23, wherein the data processing station reverts to the sixth database for the purpose of automatically selecting exercises, usable to treat capabilities in need of treatment which belong to that skill to be treated which has the highest prioritization.

25. The system as claimed in claim 13, wherein the data processing station is coupled to a another database containing a plurality of skills and a prioritization for the skills, and wherein the module is designed for automatically selecting exercises by reverting to the another database, the exercises being able to be used to treat capabilities in need of treatment which belong to that skill to be treated which has the highest prioritization.

26. The system as claimed in claim 25, wherein the module allows the prioritization to be altered by the user.

27. The system as claimed in claim 14, wherein the data processing station is coupled to a another database containing a plurality of patient physiological skills and a prioritization for the skills, and wherein the module is designed for automatically selecting exercises by reverting to the another database, the exercises being able to be used to treat capabilities in need of treatment which belong to that skill to be treated which has the highest prioritization.

28. The system as claimed in claim 27, wherein the module allows the prioritization to be altered by the user.

29. A method for supporting therapy planning when creating a training program, wherein a capability profile for a patient, a first database, and a second database, said second database containing;
   evaluating a patient's capability profile for at least one treatable patient physiological skill based upon information in a first database, including a plurality of physiological skills and an allocation of minimum prerequisites for capabilities required for a respective physiological skill, to ascertain the existing capabilities and capability deficits;
   selecting at least one exercise and capability to be treated based upon information in a second database, the second database including a plurality of patient physiological skills with expert rules relating to the selection of at least one of exercises and capabilities to be treated and including at least one of an associated order and weighting for the at least one of exercises and capabilities for determining successful acquisition of said respective patient physiological skills, taking into account existing capabilities and capability deficits of said patient, wherein the selecting takes into account the expert rules; and outputting the at least one selected exercise and capability to be treated, with associated information about at least one of the weighting and order for incorporation into a patient rehabilitation treatment plan.

30. The method as claimed in claim 29, wherein a patient physiological skill is an activity associated with for said patient enabling a patient to live an autonomous and independent life, and further comprising providing a rehabilitation skills profile for the patient from which skills that are to be treated are ascertainable.

31. The method as claimed in claim 30, wherein at least one of the patient's capability and skills profile is retrieved from at least one of a third and a fourth database.

32. The method as claimed in claim 29, wherein at least one associated target capability identifying successful acquisition of said patient skill provided in said patient rehabilitation plan is output for each exercise that is output.

33. The method as claimed in claim 32, wherein the at least one associated target capability is retrieved from another database, containing a plurality of exercises and an allocation of target capabilities which are trained when performing the respective exercise.

34. The method as claimed in claim 33, wherein a further database is provided which contains a plurality of patient physiological skills and a prioritization of the skills.

35. The method as claimed in claim 34, wherein the prioritization of the patient physiological skills in the further database is alterable by a user.

36. The method as claimed in claim 34, wherein the further database is accessed for the purpose of selecting exercises, usable to treat capabilities in need of treatment which belong to that skill to be treated which has the highest prioritization.

37. The method as claimed in claim 29, wherein the expert rules in the second database, relating to at least one of the selection of exercises and capabilities to be treated and also their at least one of order and weighting, are designed for the fastest possible acquisition of the respective skills.

38. The method as claimed in claim 29, wherein, for all at least one of exercises and capabilities to be treated, at least one of an associated organization unit and organization category is output, which is responsible for at least one of carrying out the exercise and treating the capability.

39. The method as claimed in claim 29, wherein, in the course of therapy, a current capability profile for the patient is repeatedly provided for the purpose of automatically generating proposals for modifying the training program by reverting to the expert rules in the second database again when individual capabilities change.

* * * * *